United States Patent
Tanaka

(10) Patent No.: US 7,392,233 B2
(45) Date of Patent: Jun. 24, 2008

(54) IMAGE SEARCHING SYSTEM, IMAGE SEARCHING METHOD, AND A RECORDING MEDIUM STORING AN IMAGE SEARCHING PROGRAM

(75) Inventor: Sumiyo Tanaka, Osaka (JP)

(73) Assignee: Minolta Co., Ltd., Osaka (JP)

( * ) Notice: Subject to any disclaimer, the term of this patent is extended or adjusted under 35 U.S.C. 154(b) by 1255 days.

(21) Appl. No.: 09/255,352

(22) Filed: Feb. 23, 1999

(65) Prior Publication Data

US 2002/0178135 A1  Nov. 28, 2002

(30) Foreign Application Priority Data

Feb. 24, 1998 (JP) ................. 10-041989

(51) Int. Cl.
*G06F 7/00* (2006.01)
*G06F 17/30* (2006.01)
(52) U.S. Cl. .................... 707/1; 707/3; 707/5
(58) Field of Classification Search ............ 382/284, 382/170, 236; 358/19; 345/473; 705/9; 707/1–10, 104, 508, 104.1
See application file for complete search history.

(56) References Cited

U.S. PATENT DOCUMENTS

| | | | | |
|---|---|---|---|---|
| 5,586,240 A | * | 12/1996 | Khan et al. | 707/508 |
| 5,870,741 A | * | 2/1999 | Kawabe et al. | 707/5 |
| 5,974,422 A | * | 10/1999 | Kagami et al. | 707/104 |
| 6,009,204 A | * | 12/1999 | Ahmad | 382/236 |
| 6,011,537 A | * | 1/2000 | Slotznick | 345/115 |
| 6,072,941 A | * | 6/2000 | Suzuki et al. | 395/109 |
| 6,181,818 B1 | * | 1/2001 | Sato et al. | 382/170 |
| 6,246,804 B1 | * | 6/2001 | Sato et al. | 382/284 |

FOREIGN PATENT DOCUMENTS

| | | |
|---|---|---|
| JP | 5-242160 A | 9/1993 |
| JP | 7-065169 | 3/1995 |
| JP | 7-234877 A | 9/1995 |
| JP | 8-329096 | 12/1996 |
| JP | 8-329099 A | 12/1996 |
| JP | 9-101970 A | 4/1997 |

* cited by examiner

*Primary Examiner*—Mohammad Ali
*Assistant Examiner*—Usmaan Saeed
(74) *Attorney, Agent, or Firm*—Sidley Austin LLP

(57) ABSTRACT

An image searching system, an image searching method, and a medium storing an image searching program for improving search accuracy while reducing the user burden when searching for similar images based on a plurality of key images are disclosed.

A plurality of feature quantity types is extracted from each of plural key images (S42), and feature quantities of the same type are compared between the key images to select those feature quantities having approximately equal values as the key image feature quantities to be used as search criteria (S43). Feature quantities in the target images are then extracted (S45) and a degree of similarity between the target image and key images is calculated based on a key image feature quantity and the same feature quantity in the target image (S46) Based on the resulting degree of similarity, target images having a high similarity to the key image are output as the search result (S47).

33 Claims, 9 Drawing Sheets

|  | FQ 1 | FQ 2 | FQ 3 | FQ 4 | FQ 5 |
|---|---|---|---|---|---|
| \| Image 1−Image 2 \| | 1.730 | 0.010 | 0.020 | 0.030 | 1.790 |
| \| Image 2−Image 3 \| | 2.850 | 0.000 | 0.010 | 3.400 | 1.140 |
| \| Image 1−Image 3 \| | 1.120 | 0.010 | 0.010 | 3.430 | 0.550 |
| Mean value | 1.900 | 0.007 | 0.013 | 2.287 | 1.160 |
| Flag of common FQ | 0 | 1 | 1 | 0 | 0 |

Fig.9

|  | FQ 1 | FQ 2 | FQ 3 | FQ 4 | FQ 5 |
|---|---|---|---|---|---|
| Key image 1 | 3.120 | 6.020 | 5.470 | 7.980 | 0.530 |
| Key image 2 | 4.850 | 6.010 | 5.450 | 7.950 | 2.320 |
| Key image 3 | 2.000 | 6.010 | 5.460 | 4.550 | 1.080 |
| Mean value | 3.323 | 6.013 | 5.460 | 7.827 | 1.310 |

Fig.10

|  | FQ 1 | FQ 2 | FQ 3 | FQ 4 | FQ 5 |
|---|---|---|---|---|---|
| Target image | 3.230 | 6.000 | 4.100 | 5.640 | 1.030 |

Fig.11

|  | Mean value of common FQ | Target image |
|---|---|---|
| FQ 2 | 6.013 | 0.013 |
| FQ 3 | 5.460 | 1.360 |
| Distance | — | 1.360 |
| Degree of similarity | — | 0.735 ~a |

Fig.14

|  | Key image 1 | Key image 2 | Key image 3 |
|---|---|---|---|
| Distance of FQ 1 | 0.110 | 1.620 | 1.230 |
| Distance of FQ 2 | 0.020 | 0.010 | 0.010 |
| Distance of FQ 3 | 1.370 | 1.350 | 1.360 |
| Distance of FQ 4 | 2.340 | 2.310 | 1.090 |
| Distance of FQ 5 | 0.500 | 1.290 | 0.050 |
| Distance | 2.760 | 3.383 | 2.186 |
| Degree of similarity | 0.3623 | 0.296 | 0.457 ⟵ b |

Fig.15

|  | a | Weight | Weighted degree of similarity |
|---|---|---|---|
| Degree of similarity of common FQ | 0.735 | 1.500 | 1.103 |
| Degree of similarity of all FQs | 0.457 | 1.000 | 0.457 |
| Degree of similarity | — | — | 0.624 | b, c

IMAGE SEARCHING SYSTEM, IMAGE SEARCHING METHOD, AND A RECORDING MEDIUM STORING AN IMAGE SEARCHING PROGRAM

BACKGROUND OF THE INVENTION

1. Field of the Invention

The present invention relates generally to an image searching system for finding an image that resembles a specified image from among images managed by the image searching system where the search criteria are determined from the specified image. The present invention relates more specifically to an image searching system for finding an image based on a plurality of specified images.

2. Description of the Related Art

Images stored to a database for managing image data are typically stored with additional information that can be used to specify search conditions, including search keys, such as identifying keywords and image color keys, and image features, such as information on the shapes and colors appearing in the image. Using this common type of image database, it is possible to search the stored images to find an image similar to a user-specified image.

Image similarity in similar-image searching is determined based on such feature quantities as image shape, texture, and color. More specifically, the user specifies an image in the image database that is similar to a desired image to be searched for. Feature quantities are then extracted from the image selected by the user as the search key (referred to below as the "key image"), and the extracted feature quantities are then compared with the feature quantities registered in the image database. Image similarity indicative of the similarity between the key image and a found image is then calculated. Information on any stored image determined to resemble the key image based on this calculated image similarity is then returned as the search result.

Usually there is only one key image selected by the user, and it is often impossible to find the one image sought by the user based on the feature quantities defined from a single key image. Search accuracy is therefore often low. This can happen, for example, when there are plural features in a single image and the user focuses on only one feature, that is, when the user's search criteria are narrower than the criteria that can be extracted from the key image, as well as when numerous search conditions are specified to broaden the range of the search.

Japanese Patent Laid-Open Publication 7-65169 teaches one method proposing to solve this problem. According to the taught method, a plurality of key images is specified, a specific area in each of the key images is selected, and the features to be used as search criteria are extracted from the selected areas. The search is then conducted using these features from plural selected areas in plural images. This method thus makes it possible to search for images having all of the features found in the specified areas of the plural key images. In other words, this method enables the user to specify a wide range of search conditions based on plural images.

The drawback to said taught method is that the user is required to specify in each of the selected key images those features that are to be used for searching, and this task becomes increasingly difficult and time-consuming as the number of key images increases and the variety of selected features increases.

The present invention is therefore directed to an image searching system and an image searching method for reducing the user burden and improving search accuracy when a plurality of key images is specified and a desired image is searched for based on these selected key images.

The present invention is further directed to a recording medium for storing an image searching program embodying the image searching method of the present invention.

SUMMARY OF THE INVENTION

A first image searching system according to the present invention comprises: an image storage means for storing a plurality of target images for searching; a selection means for selecting a plurality of key images for determining the search criteria; a first feature quantity extraction means for extracting one or a plurality of feature quantities from each of the plurality of key images selected by the selection means; a second feature quantity extraction means for extracting one or a plurality of feature quantities from a target image; a feature quantity identification means for comparing a feature quantity extracted by the first feature quantity extraction means with the same type of feature quantity in each of the plurality of key images to determine a feature quantity to be used for searching; a degree of similarity calculating means for calculating a degree of similarity between a target image and key image using the feature quantity identified by the feature quantity identification means for searching; and an extraction means for extracting as an image similar to a key image any target image for which the degree of similarity calculated by the degree of similarity calculating means exceeds a specific value.

Thus comprised, this first image searching system compares features extracted from plural key images to determine the features to be used as search criteria, and then calculates image similarity using the identified features (feature quantities).

In this first image searching system, the feature quantity identification means preferably defines as a feature quantity type to be used for searching a feature quantity type having an approximately equal value in each of the compared key images.

A second image searching system according to the present invention comprises: an image storage means for storing a plurality of target images for searching; a selection means for selecting a plurality of key images for determining the search criteria; a first feature quantity extraction means for extracting a feature quantity from each of the plurality of key images selected by the selection means; a second feature quantity extraction means for extracting a feature quantity from a target image; a first degree of similarity calculating means for calculating a first degree of similarity indicative of the similarity between a target image and all of the plurality of key images using the feature quantities extracted by the first and second feature quantity extraction means; a second degree of similarity calculating means for calculating a second degree of similarity indicative of the similarity between a target image and at least one of the plurality of key images using the feature quantities extracted by the first and second feature quantity extraction means; a third degree of similarity calculating means for calculating a third degree of similarity from the first and second degrees of similarity where the first degree of similarity is weighted greater than the second degree of similarity; and an extraction means for extracting as an image similar to a key image any target image for which the third degree of similarity calculated by the third degree of similarity calculating means exceeds a specific value. The third degree of similarity in this case is calculated with greater weight assigned to the first degree of similarity than to the second degree of similarity.

A first image searching method according to the present invention searches in a plurality of stored target images for an image that is similar to a key image based on the key image. This first image searching method comprises: a selection step for selecting a plurality of key images; a first feature quantity extraction step for extracting one or a plurality of feature quantity types from each of the plurality of selected key images; a second feature quantity extraction step for extracting one or a plurality of feature quantity types from the target images; a feature quantity identification step for comparing a feature quantity extracted by the first feature quantity extraction step with the same type of feature quantity in each of the plurality of key images to determine a feature quantity type to be used for searching; a degree of similarity calculating step for calculating a degree of similarity between a target image and key image using the feature quantity type identified for searching; and an extraction step for extracting as an image similar to a key image any target image for which the calculated degree of similarity exceeds a specific value.

A second image searching method for searching in a plurality of stored target images for an image that is similar to a key image based on said key image comprises: a selection step for selecting a plurality of key images; a first feature quantity extraction step for extracting a feature quantity from each of the plurality of selected key images; a second feature quantity extraction step for extracting a feature quantity from a target image; a first degree of similarity calculating step for calculating a first degree of similarity indicative of the similarity between a target image and all of the plurality of key images using the feature quantities extracted by the first and second feature quantity extraction steps; a second degree of similarity calculating means for calculating a second degree of similarity indicative of the similarity between a target image and at least one of the plurality of key images using the feature quantities extracted by the first and second feature quantity extraction steps; a third degree of similarity calculating step for calculating a third degree of similarity from the first and second degrees of similarity where the first degree of similarity is weighted greater than the second degree of similarity; and an extraction step for extracting as an image similar to a key image any target image for which the third degree of similarity exceeds a specific value.

A first recording medium according to the present invention is a computer-readable recording medium for recording an image searching program where the image searching program embodies a method for searching in a plurality of stored target images for an image that is similar to a key image based on said key image. Specific steps in this image searching program include: a selection step for selecting a plurality of key images; a first feature quantity extraction step for extracting one or a plurality of feature quantity types from each of the plurality of selected key images; a second feature quantity extraction step for extracting one or a plurality of feature quantity types from the target images; a feature quantity identification step for comparing a feature quantity extracted by the first feature quantity extraction step with the same type of feature quantity in each of the plurality of key images to determine a feature quantity type to be used for searching; a degree of similarity calculating step for calculating a degree of similarity between a target image and key image using the feature quantity type identified for searching; and an extraction step for extracting as an image similar to a key image any target image for which the calculated degree of similarity exceeds a specific value.

A second recording medium according to the present invention is also a computer-readable recording medium for recording an image searching program. Specific steps in this image searching program include: a selection step for selecting a plurality of key images; a first feature quantity extraction step for extracting a feature quantity from each of the plurality of selected key images; a second feature quantity extraction step for extracting a feature quantity from a target image; a first degree of similarity calculating step for calculating a first degree of similarity indicative of the similarity between a target image and all of the plurality of key images using the feature quantities extracted by the first and second feature quantity extraction steps; a second degree of similarity calculating means for calculating a second degree of similarity indicative of the similarity between a target image and at least one of the plurality of key images using the feature quantities extracted by the first and second feature quantity extraction steps; a second degree of similarity calculating means for calculating a second degree of similarity indicative of the similarity between a target image and at least one of the plurality of key images using the feature quantities extracted by the first and second feature quantity extraction steps; a third degree of similarity calculating step for calculating a third degree of similarity from the first and second degrees of similarity where the first degree of similarity is weighted greater than the second degree of similarity; and an extraction step for extracting as an image similar to a key image any target image for which the third degree of similarity exceeds a specific value.

BRIEF DESCRIPTION OF THE DRAWINGS

These and other objects and features of the present invention will be readily understood from the following detailed description taken in conjunction with preferred embodiments thereof with reference to the accompanying drawings, in which like parts are designated by like reference numerals and in which:

FIG. 9 is a data table of sample feature quantities extracted from a key image;

FIG. 10 is a data table of sample feature quantities extracted from a target image;

FIG. 11 is a data table used to describe similarity calculation based on common feature quantities;

FIG. 14 is a data table used to describe similarity calculation based on all feature quantities;

FIG. 15 is a data table used to describe similarity calculation based on a degree of similarity based on common feature quantities and a degree of similarity based on all feature quantities.

DESCRIPTION OF THE PREFERRED EMBODIMENTS

The preferred embodiments of an image searching system according to the present invention are described below with reference to the accompanying figures. An image searching system according to the present invention searches for an image similar to common features found in a plurality of specified key images. The image searching system extracts one or a plurality of feature quantities from the plural key images and compares similar feature quantities in the key images to determine the types of feature quantities to use for searching. The degree of similarity is then calculated using the specified feature quantity types, and an image search is then conducted based on this degree of similarity. It is therefore possible to search for images having features common to a plurality of key images.

The image searching system of the present invention can alternatively calculate the degree of similarity using both a degree of similarity indicative of the resemblance to all of the plural key images, and a degree of similarity indicative of the resemblance to one or some larger subset of the plural key images. This method makes it possible to expand the range of the search, and thus improve search accuracy.

Overall Configuration of the Image Searching System

Figure 1:
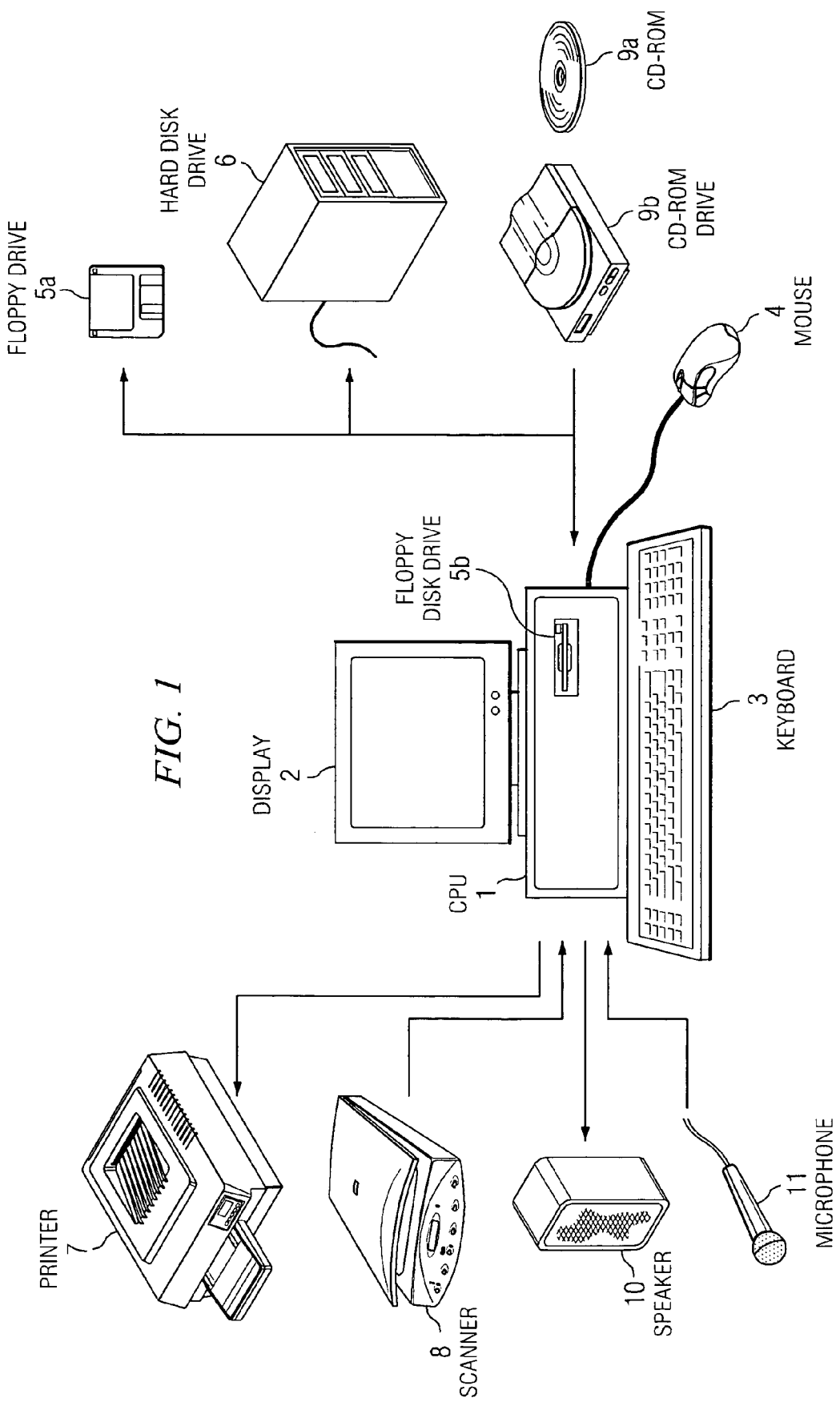
FIG. 1 is a typical overview of an image searching system according to a preferred embodiment of the present invention.

FIG. 1 shows the basic configuration of an image searching system, referred to as the "system" below, according to a preferred embodiment of the present invention. As will be known from FIG. 1, this system is built around a control device 1 for controlling the overall system and comprising a central processing unit (CPU). Connected to this exemplary control device 1 are: a display 2 for displaying text and images, as well as control prompts and other interface elements; a keyboard 3 and mouse 4 for data entry and operating the system; a floppy disk drive 5b in which a floppy disk 5a can be used and a hard disk drive 6 for reading and writing data to a data storage medium; a printer 7 for printing text and images to hard copy; a scanner 8 for capturing image data; a CD-ROM drive 9b for accessing data stored to a CD-ROM 9a; a speaker 10 for audio output; and a microphone 11 for audio input.

Figure 2:
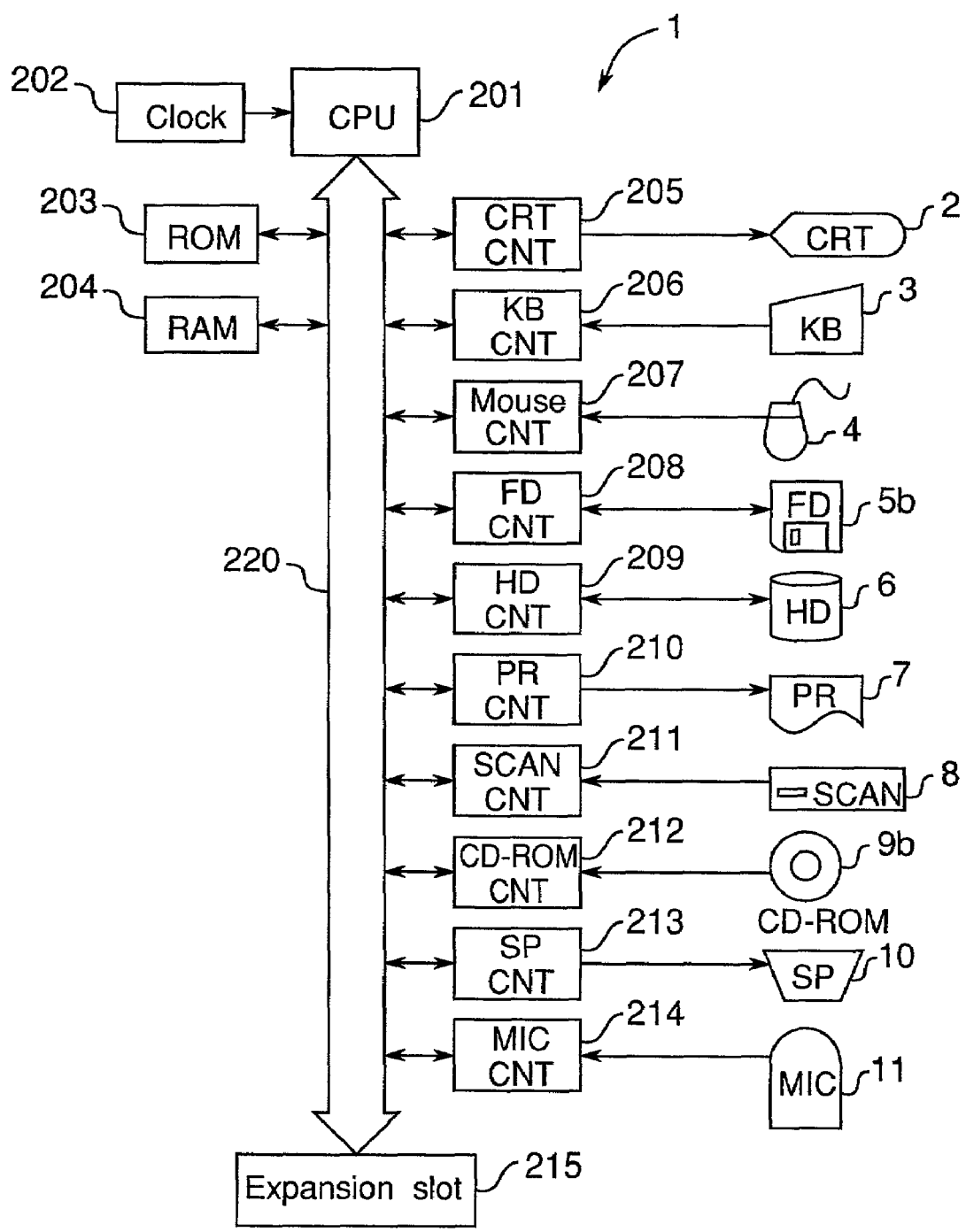
FIG. 2 is a block diagram of primarily the control device of the image searching system shown in FIG. 1.

FIG. 2 is a block diagram of the image searching system shown in FIG. 1.

Connected directly to the CPU 201 is a clock 202 for generating the reference clock required to regulate system operations. A ROM 203 for storing an application program for controlling the image searching system, and a RAM 204 for temporarily storing data and programs used by the CPU 201 for system control, are connected to the CPU 201 via a data bus 220. Circuits connected to the CPU 201 via the data bus 220 include: a display control circuit 205 for controlling the display 2 to display text and graphics; a keyboard control circuit 206 for controlling transfer of input from the keyboard 3; a mouse control circuit 207 for controlling transfer of input from the mouse 4; a floppy disk drive control circuit 208 for controlling the floppy disk drive 5b; a hard disk drive control circuit 209 for controlling the hard disk drive 6; a printer control circuit 210 for controlling output to the printer 7; a scanner control circuit 211 for controlling the scanner 8; a CD-ROM drive control circuit 212 for controlling the CD-ROM drive 9b; a speaker control circuit 213 for controlling the speaker 10; and a microphone control circuit 214 for controlling the microphone 11. An expansion slot 215 for connecting different types of system expansion boards is also connected via the data bus 220.

It should be noted that a SCSI board, for example, can be connected to the expansion slot 215 and used for connecting a floppy disk drive 5b, hard disk drive 6, scanner 8, CD-ROM drive 9b, or other device.

It should also be noted that while a floppy disk 5a and hard disk drive 6 are the preferred image data storage means in this exemplary system, the invention shall obviously not be limited thereto as any other data storage medium that the system can use can be used for image data storage, including magneto-optical (MO) disks [and DVD disks].

Furthermore, while a scanner 8 is used in this exemplary system for image data capture and input, other data input devices can also be used, including video still cameras and digital cameras.

In addition, while a printer 7 is used as an output device, a digital photocopier or other type of hard copy output device can also be used.

A program embodying the control method of the present invention is also stored to ROM 203 in this preferred embodiment. This control program, however, can be alternatively stored in whole or in part to another data storage medium, including a floppy disk 5a, hard disk drive 6, or CD-ROM 9a. In this case, the required data and program content can be read from the data storage medium as needed, buffered to RAM 204, and executed from RAM 204.

Image Database

To store and manage image data, an image searching system according to this preferred embodiment also has an image database and a color space table. The image database contains both the image data and additional information used for the search keys. The color space table is referenced when extracting color features from an image. Both the image database and color space table are logic objects stored on the hard disk drive 6 or other data storage medium.

Figure 3:
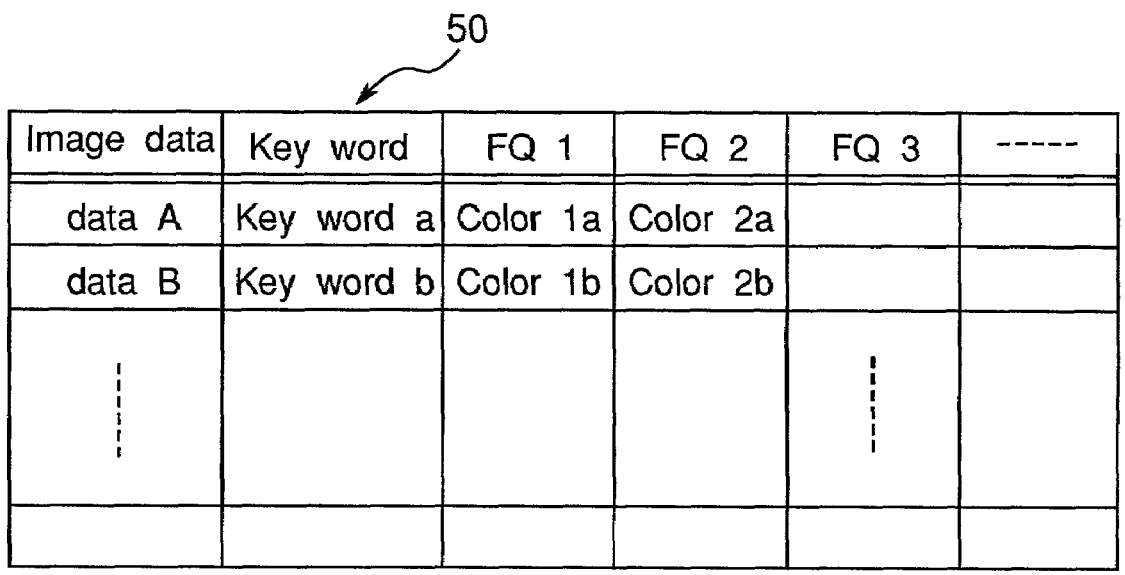
FIG. 3 shows a typical image database table structure.

An exemplary image database 50 in the present system is shown in FIG. 3. As will be known from FIG. 3, this image database 50 manages the image data to be searched, and various columns of image attributes that are used as search parameters for finding desired image data. These image attributes include keywords, a color key, and other search keys, and various feature quantities indicative of specific features in the image data. More specifically, these feature quantities include a color feature indicative of features relating to image color, a shape feature indicative of shapes in the image, and a texture feature indicative of texture patterns. The similarity between images is calculated based on this feature information.

Controlling the Image Searching System

A specific method of controlling the above-described image searching system is described next below with reference to the accompanying flow charts.

Main Loop of the Control Program

Figure 4:
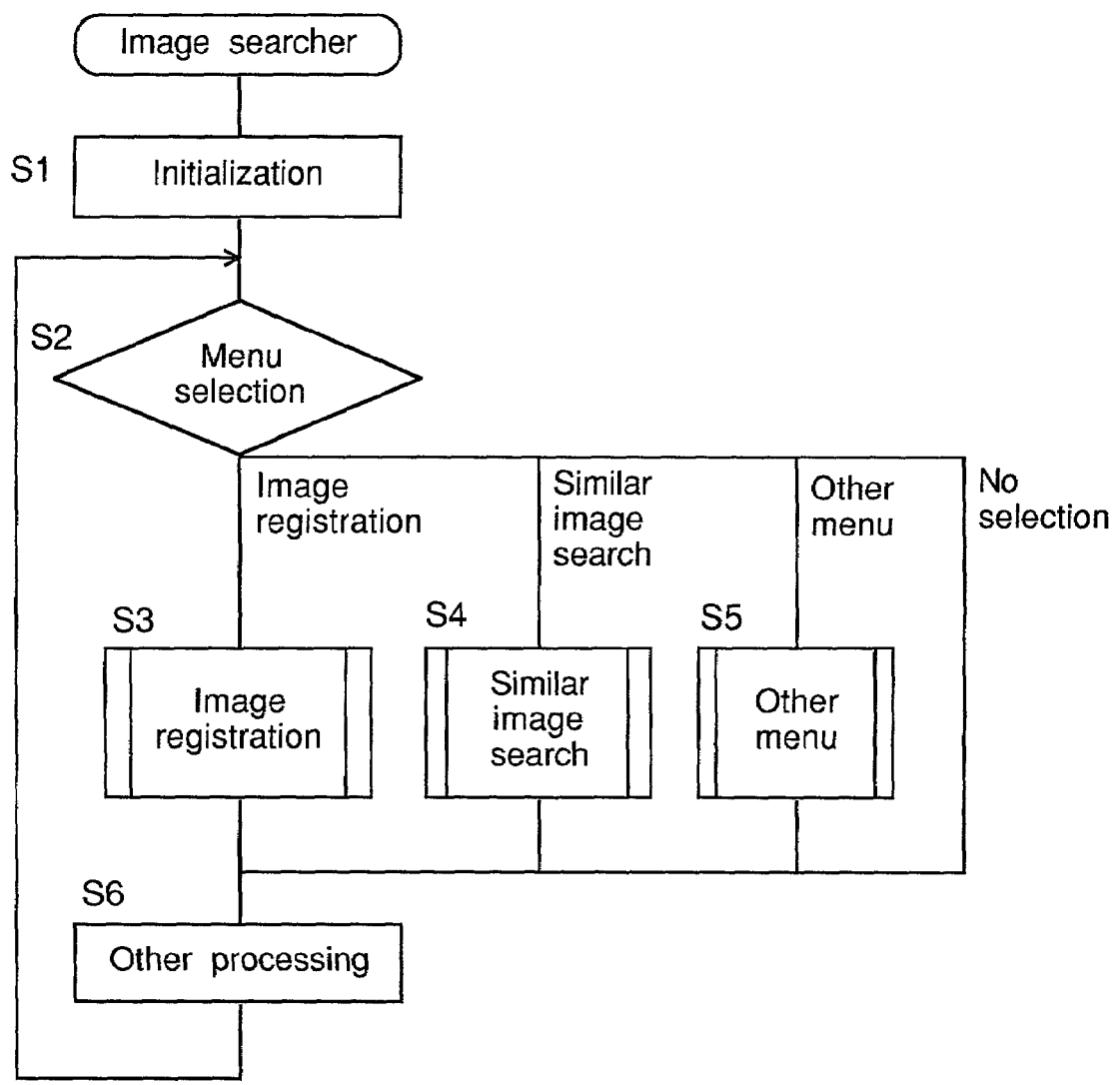
FIG. 4 is a flow chart of the main loop of the image searching method embodied in the image searching system shown in FIG. 1.

FIG. 4 is a flow chart of the main loop of a control program run by the CPU 201 in the image searching system shown in FIG. 1.

The procedure starts by initializing the various flags and variables used in the rest of the procedure, and to display the default menus (S1). An exemplary default menu screen displays various icons representing and used for selecting specific processes such that when a user selects one of the icons, the corresponding process is executed. It should be further noted that the system of this preferred embodiment enables the operator to select various processes and enter information using the keyboard 3 and mouse 4 from the default menu screen and other screens that are displayed on the display 2. After initialization in step S1, decision diamond S2 detects whether the user has selected a menu item from the default menu screen (S2).

If in step S2 the user selects "register image," for example, the image registration process (S3) is selected and run, and the procedure then advances to step S6. This image registration process (S3) is run to store image data and related feature information in the image database 50, and is described in further detail below with reference to the flow chart in FIG. 5.

If in step S2 the user selects "search for similar image," for example, the similar image searching process (S4) is selected and run, and the procedure then advances to step S6. This similar image searching process (S4) is run to search in the image database 50 for an image similar to a selected key image, and is described in further detail below with reference to the flow chart in FIG. 6.

If in step S2 the user selects another menu item, the corresponding process (S5) is selected and run, and the procedure then advances to step S6.

If no menu item is selected in S2, the procedure advances directly to step S6. After the procedure defined for step S6 is run and completed, the main loop returns to step S2 and repeats.

It should be noted that the tasks that might be performed as the "other menu process" selected in S5 are not unique to or directly related to the present invention, and further description thereof is thus omitted below. The image registration process (S3) and the similar image searching process (S4) of the present invention are described next in detail below.

Image Registration Process

Figure 5:
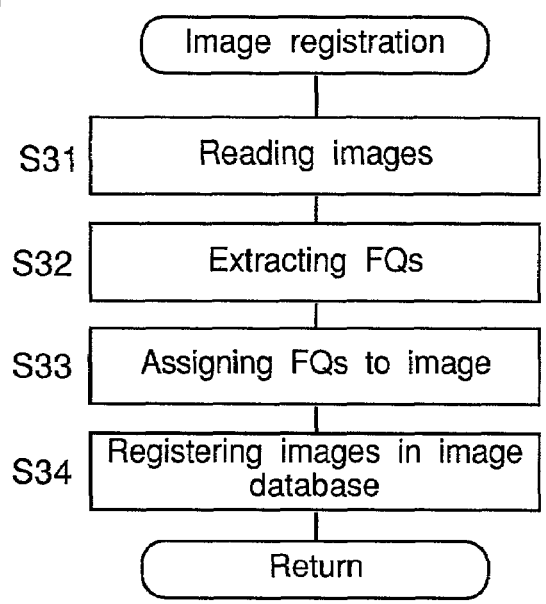
FIG. 5 is a flow chart of the image registration process shown as step S3 in FIG. 4.

The image registration process shown as step S3 in FIG. 4 is described next in detail below with reference to the flow chart in FIG. 5. This process extracts feature quantities from a user-specified image to be stored in the image database, and then stores the specified image and extracted features to the image database 50.

This routine starts by reading the user-specified image to be stored to the image database 50 (S31). A feature extraction process is then run (S32) to extract feature quantities from the specified image. In this preferred embodiment of the invention, the extracted feature quantities include color, shape, and texture, but the invention shall obviously not be limited thereto. The extracted feature quantities are then related* to the image data of the specified image (S33), and finally registered in the image database 50 together with the related specified image data (S34). A file name, image size information, and other image attributes are also normally stored with or related to the image data. The procedure then returns to the main loop (step S6 in FIG. 4).

[* NOTE: I've used "related" here because the database could be a flat file or relational database, and "related" will cover the association between feature quantities and image data for both database types (the tables in the illustrations seem to imply a flat-file (non-relational) database structure).]

Similar Image Searching Processing (a) Similar Image Search Based on Common Feature Quantities (First Embodiment)

According to first embodiment, common feature quantities are extracted from a plurality of key images. Upon evaluating a similarity of a target image to a key image, only these common feature quantities are used for calculating a degree of similarity of the target image to a key image. In other words, feature quantities other than the common feature quantities are not used for calculation of the degree of similarity.

The similar image searching processing according to first embodiment (shown as step 4 in FIG. 4) is described below with reference to a flow chart shown in FIG. 6. In the present processing, predetermined feature quantities are extracted from each of plural key images specified by a user and feature quantities indicative of features common to the plural key images are selected as common feature quantities among the extracted feature quantities. Then, the searching processing is performed to find out an image similar to a key image among images registered in the image database 50 based on the common feature quantities.

Figure 6:
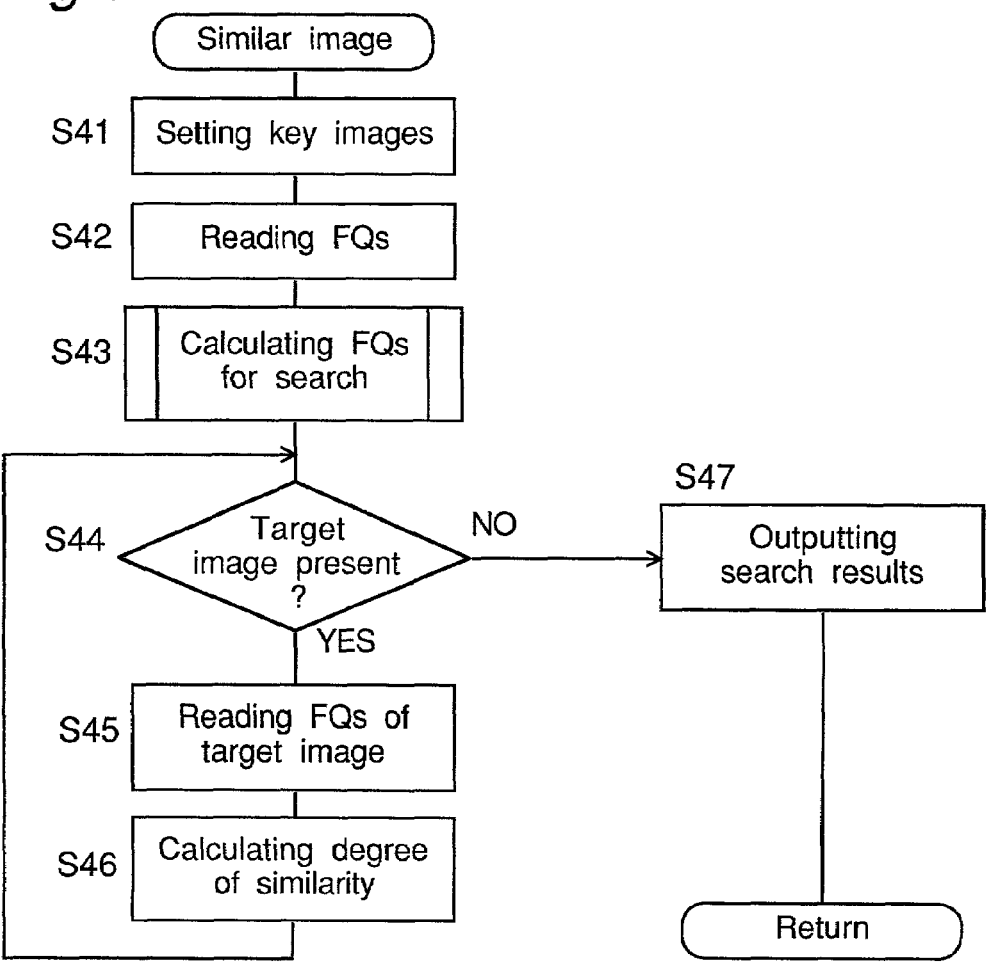
FIG. 6 is a flow chart of the similar image searching process shown as step S4 in FIG. 4.

Referring to FIG. 6, at first, a plurality of key images specified by a user are read (step S41). Feature quantities of each key image are extracted from the image database 50 (step S42). In this step, feature quantities of plural kinds such as color, shape, texture and so on are obtained from each key image. Next, a search feature quantity compilation processing is performed to calculate common feature quantities for searching a similar image by comparing the feature quantities of respective key images with each other (step S43). This search feature quantity compilation processing will be described later.

Thereafter, to find an image among images registered in the image database 50 which is similar to the key images, the common feature quantities calculated in step S43 are compared with feature quantities of each image registered in the image database, and the degree of similarity between the key images and the presently selected image is calculated (from step S44 to step S46).

Namely, it is determined if there is an image in the image database 50 for which the degree of similarity to the key images has not yet been calculated (herein below referred to as a "target image") (step S44). If such a target image is present in the image database 50, the feature quantities for that target image are read from the image database 50 (step S45). Then, a degree of similarity indicative of a similarity between the target image and each key image is calculated based on the common feature quantities of the key images and the feature quantities of the key images and the feature quantities of the target image (step S46) and the processing loops back to step S43. This calculation processing of the degree of similarity will be described later. These steps S43 to S45 are repeated until the similarity calculation has been completed for all target images in the image database.

When the degree of similarity has been calculated for all target images in the image database 50, an output processing of search results is performed (step S47) and the processing returns to the main routine. In the output processing of the search results, it is determined that those target images for which the calculated degree of similarity exceeds a predetermined threshold value are similar to the key images. The target images determined to be similar are then displayed on screen in turn from the highest degree of similarity.

Alternately, without providing any threshold for determination of the similarity, a predetermined number of target images can be displayed in a descending order from the highest degree of similarity. Further, the search results can be displayed by simply outputting the file name of the target image data, preferably with related attributes such as its location in the database. The target images tested by the search loop from step S44 to step S46 shall also not be limited to all of the images stored in the image database 50. For instance, only images preselected based on predetermined conditions can be tested.

The search feature quantity compilation processing (step S43 in FIG. 6) is described next with reference to a flow chart shown in FIG. 7. This processing calculates the common feature quantities to be used upon searching a target image which is similar in common to a plurality of key images. That is, the common feature quantities indicative of features in common to a plurality of key images are obtained by comparing feature quantities of the same kind among the plurality of key images and choosing feature quantities of the same kind having values being approximate to each other as the common feature quantities. This processing is described in further detail below.

Figures 7, 8:
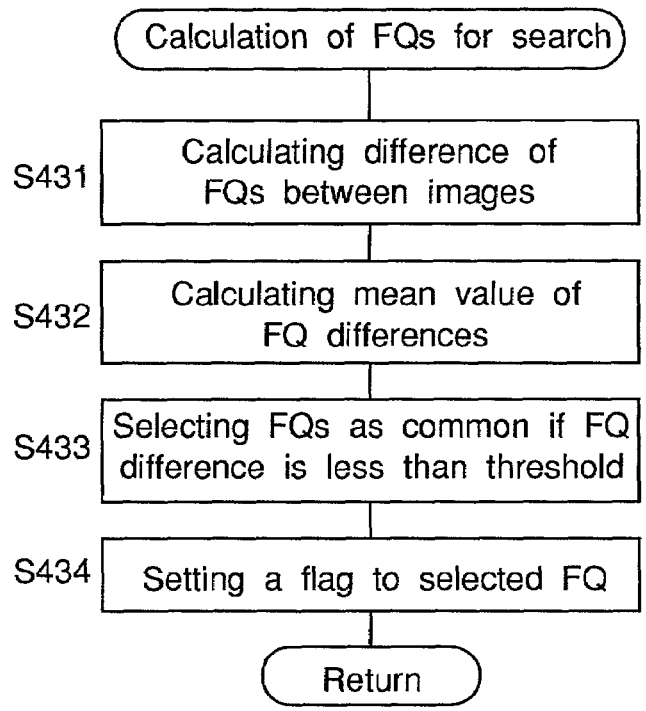
FIG. 7 is a flow chart of the search feature compilation process shown as step S43 in FIG. 6.
FIG. 8 is a data table used to describe a method of calculating common features.

As shown in FIG. 7, the processing starts by calculating, for every kind of the feature quantity, differences among the feature quantities of the key images (step S431). Next, a mean value of the differences obtained in step S431 is calculated for every kind of the feature quantity (S432). An example of this calculation is shown in FIG. 8. This figure shows an example obtained for three key images 1 to 3 each having five feature quantities 1 to 5 as shown in FIG. 9. The mean value of the differences with respect to the same feature quantity indicates the smaller the mean value the greater the image similarity with respect to that feature quantity.

Thereafter, every feature quantity or the kind of the feature quantity having a mean value equal to or less than a predetermined threshold is selected as a common feature quantity (step S433). That is, when the mean feature quantity difference is less than the threshold value, that feature quantity is determined to be common to the plural key images. In the example shown in FIG. 8, this threshold value is set to 0.1 and feature quantity 2 and feature quantity 3 are thus selected as common feature quantities. Thus, the feature quantities or kinds of feature quantities to be used for searching are determined by comparing feature quantities of the same kind in the key images. In the last step, a specific flag is set for every feature quantity selected as a common feature quantity (step S434).

Next, the processing for calculating the degree of similarity (step S46 in FIG. 6) is described below. Based on the common features extracted from the key images and a target image, this processing calculates the degree of similarity of the target image to all key images or any one of them.

According to the present embodiment, only feature quantities selected as common feature quantities in step S43 are used for calculating the degree of similarity of the target image to the key image.

Accordingly, features other than common features are not used for the calculation of the degree of similarity. Due to this, images having features common to plural key images can be obtained as the results of the search with a high accuracy. In this case, the target image is similar to all of the plural key images. In other words, this search method imposes a search under an AND condition among the key images and thereby, enables a user to restrict ranges of searching conditions to reasonable ones.

FIG. 11 shows an example of the calculation for the degree of similarity. In this example, the distance between each key image and the target image is calculated based on the values of feature quantity 2 and feature quantity 3 selected as the common features and the degree of similarity is obtained based on the calculated distances. The values shown in FIG. 11 are obtained from the following equations (1) to (3).

$$\text{Difference between features} = |(\text{key image feature quantity}) - (\text{target image feature quantity})| \quad (1)$$

$$\text{Distance} = \text{square root of } \{\text{the sum of (each feature quantity difference)}^2\} \quad (2)$$

$$\text{Degree of similarity} = 1.0/\text{distance} \quad (3)$$

The degree of similarity thus obtained indicates that the image similarity becomes high as the calculated value of the degree of similarity becomes large.

(b) Similar Image Searching Based on All Kinds of Feature Quantities (Second Embodiment)

According to a second embodiment, the degree of similarity between a target image and key images is calculated for each of the key images based on features of all kinds. From the degrees of similarity calculated for each key image, the highest degree of similarity is then selected as the degree of similarity of the target image to the corresponding key image. In this case, images similar to at least one of the plural key images are searched. That is, the image search is performed under an OR logic condition and, accordingly, it becomes possible to broaden the ranges of searching conditions by increasing the number of key images. The second embodiment performs a processing shown in FIG. 12 and FIG. 13 instead of FIGS. 6 and 7 of the first embodiment.

Figure 12:
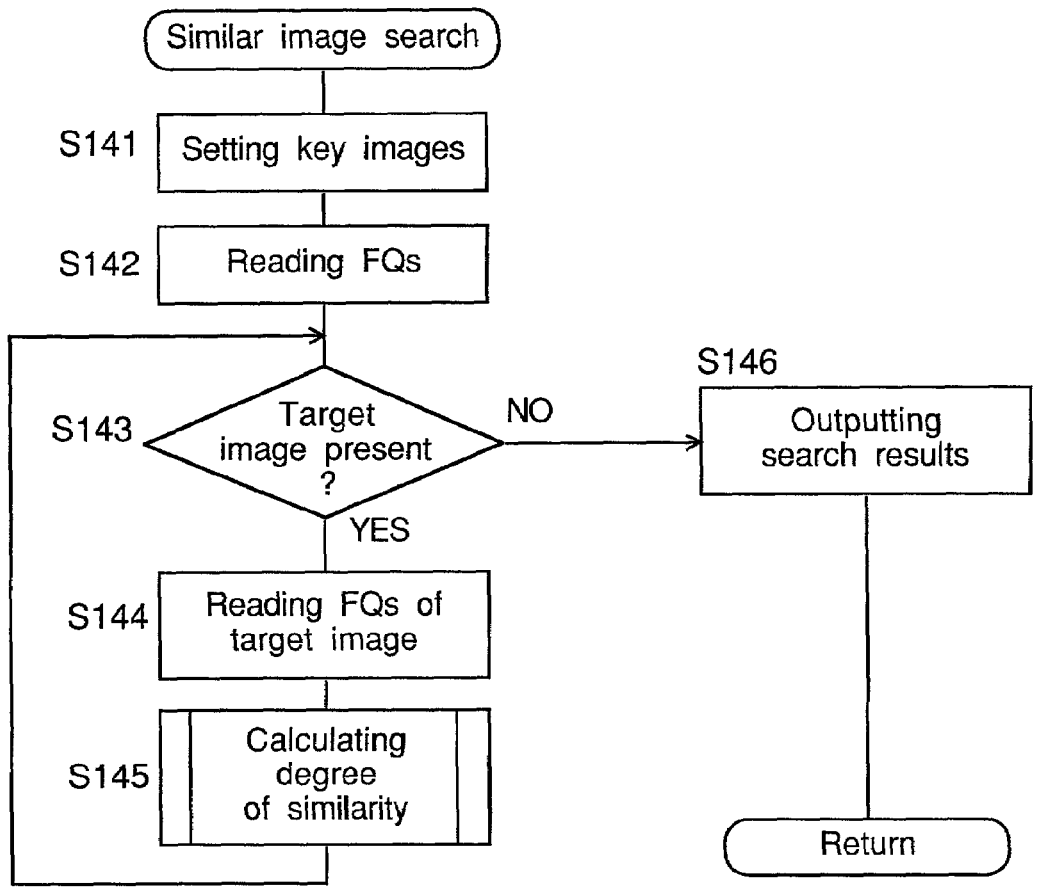
FIG. 12 is a flowchart of the similar image searching process shown as step S4 in FIG. 4, that is executed according to a second preferred embodiment of the present invention.

Referring to FIG. 12, a plurality of key images specified by a user are read (S141). Features are obtained from the image database 50 for each key image (S142). Namely, features of plural kinds such as color, shape, texture and the like are obtained from each key image.

Then, the feature quantities of each key image obtained in step S142 are compared with feature quantities of each target image registered in the image database 50, the similarity between each key image and the target image is determined and thereby, target images being similar to respective key images are searched (steps from S143 to S145).

At first, it is determined whether or not there is a target image in the image database for which the degree of similarity to each key image has not yet been calculated (step S143). If such a target image is present in the image database 50, the features for that target image are read from the image database (step S144). Then, calculation of the degree of similarity indicative of the similarity between images is performed based on the features of each key image and those of the target image (step S144). After this calculation, the processing loops back to step S143. This calculation processing of the degree of similarity (step S145) will be described later. These steps S143 to S145 are repeated until the similarity calculation has been completed for all target images in the image database 50.

When the degree of similarity has been calculated for all target images in the image database 50, an output processing of search results is performed (step S147) and then, the processing returns to the main routine. In this output processing of search results (step S146), based on the degrees of similarity calculated for all target images in the image database 50, the key image having a degree of similarity higher than a predetermined threshold value is determined to be similar to the corresponding key image. The target images determined to be similar are then display on screen in sequence from the highest degree of similarity.

Alternately, without providing any threshold for determination of the similarity, a predetermined number of target images can be displayed in a descending order from the highest degree of similarity. Further, the search results can be displayed by simply outputting the file name of the target image data, preferably with related attributes such as its location in the database. The target images tested by the search loop from step S144 to step S146 shall also not be limited to all of the images stored in the image database 50. For instance, only images preselected based on predetermined conditions can be tested.

Figure 13:
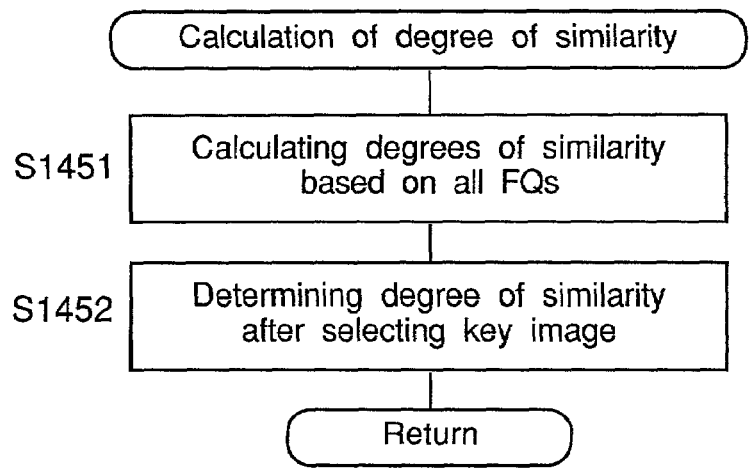
FIG. 13 is a flowchart of the search feature compilation process shown as step S43 in FIG. 6, that is executed according to the second preferred embodiment of the present invention.

Next, the calculation processing of degree of similarity is described below with reference to a flow chart shown in FIG. 13.

As shown in FIG. 14, a distance between a feature quantity of the key image and that of the same kind of the target image is calculated for each of all the features, and a distance between the key images and the target image is calculated based on the distances of respective features.

Based on the distance between images, the degree of similarity is calculated (step S1451). More specifically, the values shown in FIG. 14 are obtained from the following equations (4) to (6).

$$\text{Feature quantity distance} = |(\text{key image feature quantity}) - (\text{target image feature quantity})| \quad (4)$$

$$\text{Distance} = \text{sqrt of } \{\text{sum of (each feature quantity distance)}^2\} \quad (5)$$

$$\text{Degree of similarity} = 1.0/\text{distance}$$

Note that with this method image similarity increases as the calculated degree of similarity value rises. Because the degree of similarity to key image 3 is highest in the example shown in FIG. 14, that value is used as the degree of similarity between the current target image and the key images (step S1452).

The output processing of search results mentioned above with respect to step S146 is performed based on the degrees of similarity determined in step S1452.

(c) Similar Image Searching Processing Using Degrees of Similarity Based on All Feature Quantities and Degrees of Similarity Based on Common Feature Quantities (Third Embodiment)

This method combines the degrees of similarity based on the common feature quantities calculated according to first embodiment (a) and those based on all feature quantities calculated according to second embodiment (b), to obtain final degrees of similarity. In this case, the degree of similarity based on common feature quantities is weighted and the weighted degree of similarity and the degree of similarity based on all feature quantities are added to obtain a mean value thereof. This mean value is assigned as the degree of similarity of the target image to the key image. Thus, this method performs a similar image search in combination of AND and OR conditions. As a result, it becomes possible to find an image having features common to all key images among images similar to any one of the key images and therefore, to improve the search accuracy compared with second embodiment (b).

An example of the calculation of the degree of similarity is shown in FIG. 15. In this example, the weight for the degree of similarity a calculated in FIG. 11 is set larger than that for the degree of similarity b calculated in FIG. 14. A weighted mean value is then calculated to obtain the final degree of similarity c. This final degree of similarity c is obtained according to the next equation (7).

$$\text{Degree of similarity} = \{(\text{degree of similarity } a \times \text{weight } wa) + (\text{degree of similarity } b \times \text{weight } wb)\}/(wa+wb) \quad (7)$$

As stated above, according to the present embodiment, features are extracted from a plurality of key images, when specified and those common to the plural key images are selected to determine similarity between images using these common features. Thus, the common features are automatically determine from among plural key images and accordingly, the user burden can be reduced. It is also possible to search for images having features common to plural key images. This enables the user to narrow the ranges of respective searching conditions by specifying plural key images. Also, the search can be similarly expanded to broader ranges of searching conditions by considering the degree of similarity indicating similarity of an image to at least one of plural key images. Search accuracy can be thus improved.

As will be known from the above descriptions of the present invention, a first image searching system, a first image searching method, and a first recording medium storing an image searching program embodying the first image searching method of the invention determines the feature quantities to be used for image searching based on the feature quantities extracted from one or more key images, and calculates a degree of similarity using only the feature quantities selected as search criteria. It is therefore possible to search for images with features common to those of the selected key images. The search conditions can thus be restricted by specifying plural key images, and search accuracy can thus be improved. The user burden is also reduced because feature quantities are automatically extracted from the specified key images, and similar images are searched for based on the extracted feature quantities.

As will be known from the above descriptions of the present invention, a second image searching system, a second image searching method, and a second recording medium storing an image searching program embodying the second image searching method of the invention calculates the degree of similarity used for searching by combining a degree of similarity indicative of similarity to all of the plurality of key image, and a degree of similarity indicative of similarity to any one of the plurality of key image. It is therefore possible to set a wide range of search criteria by selecting a plurality of key images, and further improve the accuracy of similar image searches.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

What is claimed is:

1. An image searching system comprising:
    an image database storing a plurality of database images, each of said plurality of database images having a plurality of features;
    a specifying controller for specifying a plurality of key images, each of said plurality of key images being specified by a user and having a respective plurality of features;
    an extracting controller for extracting common key image feature values for common key image features that are common to the plurality of key images;
    a calculating controller for comparing the common key image feature values, extracted by the extracting controller, with the respective feature values of the plurality of database images to thereby sequentially calculate similarities between each of the common key image feature values and respective ones of the database image feature values for each of the plurality of database images; and a searching controller for retrieving from the database at least one of the plurality of database images which is similar to the plurality of key images, based on a similarity calculated by the calculating controller.

2. An image searching system as claimed in claim 1, wherein the extracting controller includes:
an extracting algorithm for extracting a plurality of types of features from the plurality of key images specified by the specifying controller;
a selecting algorithm for comparing the plurality of types of features extracted by the extracting algorithm, with the plurality of key images specified by the specifying controller to thereby select at least one of the types of the features; and
a determining algorithm for determining the common key image features based on the at least one type of the features selected by the selecting algorithm.

3. An image searching system as claimed in claim 2,
wherein the selecting algorithm is operable to compare common types of the features of respective ones of the plurality of key images specified by the specifying controller,
wherein the determining algorithm is operable to calculate an average similarity value for the features of the plurality of key images with respect to the at least one type of the features selected by the selecting algorithm to thereby determine the average similarity value for each of the at least one type of the features.

4. An image searching system which comprises:
an image database storing a plurality of database images to be searched, each of said plurality of database images having a plurality of database image features;
a specifying controller for specifying a plurality of key images used to specify search conditions, each of said plurality of key images being specified by a user and having a plurality of key image features, each of said plurality of key images having a common feature value for each of said plurality of key image features;
a calculating controller for comparing the plurality of key images, specified by the specifying controller, with the plurality of database images to thereby calculate similarities between the common feature value for each of the plurality of key image features and a corresponding one of the plurality of database image features for each of the plurality of database images;
a selecting controller for retrieving a particular key image from the specified plurality of key images based on the similarities calculated by the calculating controller; and
a searching controller for retrieving images from the plurality of database images based on the similarity between the particular key image, selected by the selecting controller, and the plurality of database images.

5. An image searching system as claimed in claim 4, wherein the selecting controller is operable to select as a particular one of the plurality of key images, a particular one of the plurality of key images which most resembles an image being searched for.

6. An image sensing system as claimed in claim 5,
wherein the calculating controller is operable to calculate the types of the features of the plurality of key images and then operable to calculate degrees of similarity by comparing the key image features for each of the plurality of key images with corresponding database feature quantities of the database images for each type of the features,
wherein the selecting controller selects, as the particular key image, a one of the plurality of key images which most resembles an image being searched for with respect to an average value of the degrees of similarity calculated by the calculating controller for each type of the features.

7. An image searching system which comprises:
an image database storing a plurality of database images;
a specifying controller for specifying a plurality of key images specified by a user for specifying search conditions;
a first calculating controller for comparing a feature value calculated for each common feature of the plurality of key images to thereby calculate a first degree of similarity for each of said plurality of database images;
a second calculating controller for selecting a particular key image from the plurality of key images and for comparing the particular key image with the plurality of database images to thereby calculate a second degree of similarity for each of the plurality of database images;
a third calculating controller for calculating a final degree of similarity for each of said plurality of database images for use in searching based on the first and second degrees of similarity calculated respectively by the first and second calculating controllers; and
a searching controller for retrieving at least one of the plurality of database images, which is similar to the particular key image, based on the final degree of similarity calculated by the third calculating controller for each of the plurality of database images.

8. An image searching system as claimed in claim 7, wherein the third calculating controller is operable to increase a weight of the first degree of similarity, calculated by the first calculating controller, to a value greater than that of the second degree of similarity, calculated by the second calculating controller, to thereby calculate the final degree of similarity.

9. An image searching system as claimed in claim 8, wherein the first calculating controller is operable to extract common features of the image that are common to all of the key images, and to compare those common features with respective database image features of each of the plurality of database images to thereby calculate the first degree of similarity.

10. An image searching system as claimed in claim 9, wherein the second calculating controller is operable to select from the plurality of key images a key image most similar to a desired image and to calculate the second degree of similarity for each of the database images.

11. An image searching method which comprises the steps of:
storing a plurality of database images in a database;
specifying a plurality of key images specified by a user for specifying search conditions;
extracting common feature values from the plurality of key images;
comparing the common feature values with the feature values of the plurality of database images to thereby sequentially calculate similarities between the common feature values and the database image feature values; and
retrieving from the plurality of database images at least one of the plurality of database images which is similar to the plurality of key images based on the similarities for each of the plurality of database images.

12. An image searching method as claimed in claim 11, wherein the extracting step includes the sub-steps of:
- extracting a plurality of types of features from the plurality of key images;
- comparing the features from among the plurality of key images to thereby select at least one of the types of the features; and
- determining common features based on the at least one type of the features.

13. An image searching method as claimed in claim 12,
- wherein the step of comparing includes comparing features of the plurality of key images, and
- wherein the step of determining includes calculating an average value of the features of the plurality of key images with respect to the types of the features to thereby determine a calculated average value as representing the common features.

14. An image searching method which comprises the steps of:
- storing a plurality of database images in an image database, said plurality of database images each having a plurality of database feature values;
- specifying a plurality of key images specified by a user for specifying search conditions, said plurality of key images having common features, said common features of said plurality of key images each having a key image feature value;
- comparing the key image feature values of the plurality of key images with the plurality of database feature values of the plurality of database images to thereby calculate similarities between the key image feature values and the plurality of database image feature values;
- retrieving a particular key image from the plurality of key images based on the similarities; and
- retrieving images from the database images based on the similarity between the particular key image and the plurality of database images.

15. An image searching method as claimed in claim 14,
- wherein the step of specifying includes selecting as a particular one of the specified plurality of key images the key images which most resemble the database images being searched for.

16. An image searching method as claimed in claim 15, wherein the calculating controller is operable to calculate a plurality of types of the features from the plurality of key images to derive the common feature values and then to calculate a degree of similarity by comparing the common feature values of each type of feature with corresponding feature values of the plurality of database images for each type of feature, and
- wherein the selecting controller selects, as the particular key image from the specified plurality of key images, the key images which most resemble the plurality of database images being searched with respect to an average value of degrees of similarities calculated by the calculating controller for each type of the features.

17. An image searching method which comprises the steps of:
- storing a plurality of database images in an image database;
- specifying a plurality of key images specified by a user for specifying search conditions, said plurality of key images each having a plurality of common feature values, each of said common feature values corresponding to one of the features of the plurality of key images;
- comparing the common feature values of the plurality of key images with respective feature values of the plurality of database images to thereby calculate first similarities therebetween;
- selecting a particular key image from the plurality of key images and comparing the particular key image with the plurality of database images to thereby calculate second similarities therebetween;
- calculating a final similarity for use in searching based on the first and second similarities; and
- retrieving one of the plurality of database images, which is similar to the particular key image, based on the final similarity.

18. An image searching method as claimed in claim 17, wherein the step of calculating includes a step of increasing a weight of a degree of the first similarity to a value greater than that of a degree of the second similarity to thereby calculate the final similarity.

19. An image searching method as claimed in claim 18, wherein the step of comparing includes the step of extracting the features of the image which are common to all of the key images, and comparing the common feature values of those common features with respective feature values of each of the database images to thereby calculate the first similarities.

20. An image searching method as claimed in claim 19, wherein the step of selecting includes selecting the key images most similar to the database image and to calculate the second similarity.

21. A software program including computer-executable instructions stored on a recording medium, said program comprising:
- instructions for storing a plurality of database images in a database;
- instructions for specifying a plurality of key images specified by a user for specifying search conditions;
- instructions for extracting common feature values of features of the plurality of key images;
- instructions for comparing the common feature values with feature values of the plurality of database images to thereby sequentially calculate similarities between the common feature values of the plurality of key images and the database image feature values; and
- instructions for retrieving from the plurality of database images at least one of the database images which is similar to one of the key images based on the similarities.

22. A software program including computer-executable instructions stored on a recording medium as claimed in claim 21, wherein the instruction for extracting includes an instruction for extracting a plurality of types of the features from respective key images;
- an instruction for comparing the feature values for the extracted types of features of each one of the plurality of key images with the feature values for the extracted types of features for each of the plurality of key images to thereby select at least one of the types of the features; and
- an instruction for determining the common feature values based on the at least one type of the features.

23. A software program including computer-executable instructions stored on a recording medium as claimed in claim 22,
- wherein the instruction for comparing compares the features of same types among the plurality of key images, and
- wherein the instruction for determining calculates an average value of the features of each of the plurality of key images with respect to the types of the features to thereby determine the calculated average value as the common feature values.

24. A software program including computer-executable instructions stored on a recording medium, said program comprising:
   instructions for storing a plurality of database images in an image database, wherein said instructions for storing also include instructions for storing a plurality of database image feature values for each of the plurality of database images;
   instructions for specifying a plurality of key images specified by a user having common feature values used to specify search conditions;
   instructions for comparing the plurality of key images with the plurality of database images to thereby calculate similarities between common feature values of the plurality of key images and the database image feature values;
   instructions for retrieving a particular key image from the specified plurality of key images based on the similarities; and
   instructions for retrieving images from the plurality of database images based on the similarity between the particular key image and the database images.

25. A software program including computer-executable instructions stored on a recording medium as claimed in claim 24,
   wherein the instructions for retrieving include instructions to select as the particular key image one of the plurality of key images which most resembles the database images being searched for.

26. A recording medium as claimed in claim 25,
   wherein each of said plurality of key images and each of said plurality of database images has a plurality of features associated therewith,
   wherein the instruction for comparing includes instructions to calculate a plurality of types of the features from the plurality of key images and then to calculate a degree of similarity by comparing the features of the plurality of key images with respective features of the database images for each type of the feature, and
   wherein the instructions for retrieving include instructions for selecting, as the particular key image the key image which most resembles one of the database images with respect to an average value of the similarities for each type of the features.

27. A software program including computer-executable instructions stored on a recording medium, said program comprising:
   instructions for storing a plurality of database images in an image database, said database images each having a plurality of database image feature values;
   instructions for specifying a plurality of key images specified by a user for specifying search conditions, said plurality of key images each having a plurality of features;
   instructions for calculating feature values for each of the plurality of key images from the plurality of features for each of the plurality of key images;
   instructions for comparing the feature values of each of the plurality of key images with respective feature values of the plurality of database images to thereby calculate first similarities between the feature values of the plurality of key images and the feature values of the plurality of database images;
   instructions for selecting a particular key image from the plurality of key images;
   instructions for comparing the feature values of the particular key image with the feature values of the plurality of database images to thereby calculate second similarities therebetween;
   instructions for calculating a final similarity based on the first and second similarities; and
   instructions for retrieving at least one of the plurality of database images, based on the final similarity.

28. A software program including computer-executable instructions stored on a recording medium as claimed in claim 27, wherein the instructions for calculating a final similarity for each of the database images includes instructions for increasing a weighting of the first similarities, to a value greater than that of the second similarities, to thereby calculate the final similarity.

29. A software program including computer-executable instructions stored on a recording medium as claimed in claim 28, wherein the instructions for calculating include instructions for extracting common features common to all of the key images, and include instructions for comparing those common features with the plurality of database images to thereby calculate the degree of first similarities.

30. A software program including computer-executable instructions stored on a recording medium as claimed in claim 29, wherein the instructions for calculating include instructions for selecting the key images most similar to a desired image.

31. An image searching method in an image database system storing a plurality of database images which comprises the steps of:
   specifying a plurality of key images specified by a user for specifying search conditions, said plurality of key images each having a plurality of key image features each corresponding to at least one of a plurality of database features, said plurality of key images having a plurality of common features which are common to all of the plurality of key images;
   calculating common key image feature values from the common features for each of the plurality of key images;
   comparing the common feature values of the common features with corresponding database image features of the plurality of database images to calculate similarities therebetween;
   retrieving a particular key image from the plurality of key images based on the similarities such that the particular key image retrieved is the key image which most resembles the database images being searched for; and
   retrieving images from the plurality of database images which are most similar to the particular key image based on the similarity between the particular key image and the plurality of database images.

32. A recording medium storing therein a computer-executable image searching program for searching an image database storing a plurality of database images, said program comprising:
   specifying a plurality of key images specified by a user for specifying search conditions;
   calculating common feature values of the plurality of key images by comparing the plurality of key image features for each of the key images to determine feature values which are common to all of the plurality of key images;
   comparing common feature values of the plurality of key images with the database image feature values of the plurality of database images to calculate similarities therebetween;

retrieving a particular key image from the specified plurality of key images based on the similarities; and retrieving images from the plurality of database images based on the similarity between the particular key image and the plurality of database images, wherein the particular key image is the one of the plurality of key images which most resembles a desired image.

33. An image searching method according to claim 1, wherein the similarity is determined by satisfying the following three equations:

$$FQ_{difference} = |KIFQ_a - DI_bFQ_a| \quad\quad 1)$$

where $KIFQ_a$ is the key image feature quantity for one of the a number of feature quantities, where $DI_bFQ_a$ is the database image feature quantity for one of the a number of feature quantities for one of the b number of database images;

$$FQ_{distance} = \sqrt{\Sigma(FQ_{difference})^2}; \quad\quad 2)$$

and $$similarity = 1.0/FQ_{distance}. \quad\quad 3)$$

* * * * *